United States Patent [19]

Bull

[11] Patent Number: 4,588,845

[45] Date of Patent: May 13, 1986

[54] OXIDATION OF UNSATURATED ORGANIC COMPOUNDS WITH HYDROGEN PEROXIDE

[75] Inventor: Randy A. Bull, Hopewell, N.J.

[73] Assignee: FMC Corporation, Philadelphia, Pa.

[21] Appl. No.: 613,982

[22] Filed: May 25, 1984

Related U.S. Application Data

[63] Continuation-in-part of Ser. No. 514,748, Jul. 18, 1983.

[51] Int. Cl.$^4$ ............................................. C07C 37/60
[52] U.S. Cl. ................................. 568/771; 568/800; 568/803
[58] Field of Search ............... 568/768, 803, 800, 741, 568/771; 549/531, 523; 560/131

[56] References Cited

U.S. PATENT DOCUMENTS

| | | | |
|---|---|---|---|
| 3,461,170 | 8/1969 | Schmerling | 260/613 |
| 3,580,956 | 5/1971 | Bloch | 260/621 |
| 3,816,545 | 6/1974 | Block | 568/771 |
| 3,849,502 | 11/1974 | Bourdin et al. | 260/613 D |
| 3,872,156 | 3/1975 | Bourdin et al. | 568/803 |
| 3,899,540 | 8/1975 | Suzuki et al. | 260/621 G |
| 3,914,323 | 10/1975 | Maggioni | 260/621 G |
| 3,920,756 | 11/1975 | Tahara et al. | 260/621 G |
| 3,929,913 | 12/1975 | Maggioni | 260/621 G |
| 3,943,179 | 3/1976 | Bost et al. | 260/621 G |
| 4,053,523 | 10/1977 | Seifert et al. | 260/621 G |
| 4,078,006 | 3/1978 | Umemura et al. | 260/621 G |
| 4,125,543 | 11/1978 | Lecloux et al. | 260/348.25 |
| 4,174,460 | 11/1979 | Seifert et al. | 568/771 |
| 4,182,917 | 1/1980 | Seifert et al. | 568/771 |
| 4,208,536 | 6/1980 | Costantini et al. | 568/771 |
| 4,214,105 | 7/1980 | Seifert et al. | 568/771 |
| 4,223,165 | 9/1980 | Jouffret | 568/771 |
| 4,301,307 | 11/1981 | Jouffret et al. | 568/771 |
| 4,324,925 | 4/1982 | Jupe | 568/741 |
| 4,356,318 | 10/1982 | Waller | 562/406 |

FOREIGN PATENT DOCUMENTS 2083816  3/1982  United Kingdom ............... 568/771

OTHER PUBLICATIONS

Research Disclosure 19515, Jul. 1980, pp. 70–71.
Research Disclosure 22108, Sep. 1982, p. 311.
Research Disclosure 22014, Aug. 1982, p. 280.
Research Disclosure 22016, Aug. 1982, pp. 280–281.
Rubinstein, I. and Bard, A., "Polymer Films on Electrodes. 5. Electrochemistry and Chemiluminescence at Nafion-Coated Electrodes," *J. Am. Chem. Soc.*, 103, 5007, 5013 (1981).
Condensed Chem. Dictionary pp. 28, 76, 78, 452, 643 and 676.

*Primary Examiner*—Werren B. Lone
*Attorney, Agent, or Firm*—Richard E. Elden; Robert L. Andersen

[57] ABSTRACT

A process is provided for oxidizing unsaturated organic compounds with hydrogen peroxide in the presence of a strong-acid type of polymer containing a cation of a transition metal. The process results in a decrease in undesired side reactions in epoxidations and improved isomer control in the hydroxylation of aromatic compounds.

14 Claims, No Drawings

OXIDATION OF UNSATURATED ORGANIC COMPOUNDS WITH HYDROGEN PEROXIDE

This is a continuation-in-part of copending application Ser. No. 514,748, filed July 18, 1983.

The present invention is for a process to oxidize unsaturated organic compounds with hydrogen peroxide and is particularly adaptable for the oxidation of organic compounds which are difficult to oxidize, such as the oxidation of phenols to dihydroxybenzenes.

It is well known that hydrogen peroxide can be used to oxidize many organic compounds. However, some organic compounds are more difficult to oxidize and require a catalyst or activator in addition to hydrogen peroxide. In these cases it is the catalyst or activator that determines the reactivity and also the selectivity of the oxidation. An example is the hydroxylation of phenol to dihydroxybenzene. This reaction with hydrogen peroxide as the oxidant usually requires a catalyst or activator. A ferrous catalyst results in poor selectivity, producing all three dihydroxybenzene isomers catechol, resorcinol, and hydroquinone. A strong acid catalyst produces both catechol and hydroquinone. Other known catalysts for hydrogen peroxide, such as the transition metals titanium, vanadium, and molybdenum, have no apparent effect on this hydroxylation.

Jouffret, in U.S. Pat. No. 4,223,165 which is incorporated herein in its entirety by reference, reviews the prior art disclosures. Jouffret concludes that no simple method taught by the prior art is suitable for an industrial process to introduce hydroxyl radicals into an aromatic nucleus using hydrogen peroxide as the oxidant. Jouffret teaches that it is possible to react phenols with hydrogen peroxide using trifluoromethanesulfonic acid which functions both as a solvent and as a catalyst. In addition, Jouffret finds it necessary to control the total water to less than 5%, to maintain the reaction temperature between $-40°$ C. and $10°$ C. and to complex detrimental metal ions, such as iron, copper, and vanadium. Jouffret teaches that the reaction product may contain up to 0.6 mols of catechol per mol of hydroquinone. The method of Jouffret has the disadvantage of requiring refrigeration because of the critical low temperatures and also requires the use of large amounts of expensive trifluoromethanesulfonic acid.

British Patent No. 2,083,816 teaches that a product mixture can be prepared containing 0.9 mols of catechol per mol of hydroquinone by reacting an aqueous mixture of hydrogen peroxide and phenol in the absence of a strong acid by using a catalyst composed of a titanium-modified synthetic zeolite containing boron and an organic base. However, the process of British Patent No. 2,083,816 requires a large volume of water which can be a disadvantage for an industrial scale process.

In U.S. Pat. No. 4,356,318, Waller teaches that a polymeric perfluorinated sulfonic acid is interchangable with other strong acids as a catalyst compound for carbonylation of toluene to toluic acid.

U.S. Pat. No. 4,214,105 to Seifert et al teaches a process to hydroxylate phenol using substantially anhydrous hydrogen peroxide and a strongly acid catalyst. The production of the anhydrous hydrogen peroxide solution is both a hazardous and an expensive step in the process. The Seifert et al patent also does not suggest a method to control the mol ratio of the dihydroxy phenol isomers produced.

The present invention is to a process for oxidizing an organic compound selected from the group consisting of arenes, alkenes, and cyclic ketones by contacting the organic compound with aqueous hydrogen peroxide in the presence of a strong-acid type cation exchange polymer wherein at least part of the cations are simple or complex cations of a transition metal, preferably vanadium, titanium, zirconium, or uranium.

Although any transition metal cation may be used for the process it is desirable to use a cation of a transition metal capable of forming a peroxo complex when reacted with hydrogen peroxide. The cations may be either simple ions or complex ions, including those formed as ionically, covalently, or coordinatively bound atoms or molecules as long as the complex has an overall positive charge. Examples of the latter include vanadyl and titanyl ions.

For the purpose of this invention the term "strong-acid type" polymer refers to an ion exchange polymer which will act as a strong acid (or be "strongly acid") when completely exchanged with protons.

The strong-acid type polymer can be any strong acid cation ion exchange polymer such as one containing a sulfonic acid moiety. Preferably the polymer is a perfluorinated sulfonic acid polymer. The polymer may be in any convenient form such as a liquid or a solid which can be separated readily from the reaction product by conventional separation steps. It may be desirable to have the polymer present as a membrane or in the form of tubing. A solid polymer or resin in the form of granules, agglomerates, or a powder with a large surface to volume ratio is preferred when the maximum reaction rates are desired.

Any standard procedures for ion-exchanging metal into a polymer which can result in a lightly exchanged or heavily exchanged polymer may be used. At least some of the strong acid moieties of the polymer must be associated with a transition metal cation. If desired, all the strong acid moieties can be exchanged with a transition metal to produce the catalyst. For convenience in preparation and to obtain reasonable reaction rates, a metal loading with between 1% and 80% of the sulfonate groups associated with the metal is desirable. The otherwise unassociated sulfonate groups may be in the strongly acid form or may be exchanged with another metal, such as an alkali metal cation. It may be useful to use a strong-acid type resin exchanged with more than one metal as a catalyst.

For the purpose of this invention the mol ratio of orthohydroxy aromatic to parahydroxy compound formed is termed the 0:P mol ratio. The 0:P mol ratio normally ranges from 1:1 (1) to 2:1, (2) when phenol is hydroxylated in the presence of catalytic quantities of a miscible strong acid such as trifluoromethanesulfonic acid. Unexpectedly it has been found that the 0:P mol ratio can be controlled from more than 5:1 (5.0) when the transition metal is uranium to less than 1:5 (0.2) when the transition metal is titanium.

It has been further found that the rate of reaction increases as the cations of the strong-acid type polymer are replaced with said transition metal cations.

The mol ratio of water to hydrogen peroxide present in the reaction mixture is not critical. When it is desired to minimize hydrolytic side reactions, such as to prevent the opening of an oxirane ring to form a glycol, then only a small quantity of water need be present. However, for hydroxylation reactions it may be preferred to have a relatively large amount of water present. Although the water and hydrogen peroxide may be incorporated into the reaction mixture separately it is usually convenient to add the hydrogen peroxide and water together as an aqueous solution. For the purpose of this invention the water. incorporated into the reaction mixtures will be expressed as the water in the hydrogen peroxide employed. For example, adding 1 gram of 70% $H_2O_2$ implies the incorporation of 0.3 g water. If desired the oxirane ring may be opened by hydrolysis to form a glycol according to processes well known to those familiar with the art. The process is also useful for the Baeyer-Villiger oxidation of cyclic ketones to lactones and is particularly suitable for the oxidation of cyclohexanone to caprolactone.

Although any unsaturated arene may be oxidized by the process of the present invention, the process is desirable for the oxidation of arenes which are difficult to oxidize without a catalyst. The process is also particularly desirable for the hydroxylation of aromatic rings, especially if it is desirable to control the isomeric distribution of the product. For example, the process is particularly adaptable to the process of oxidizing phenol to a dihydroxybenzene in which either the catechol or the hydroquinone isomer predominates.

Although the mechanism of the reaction is not understood, it is clear that the results are different from the results of the process taught by Jouffret in which hydrogen peroxide and phenol are reacted in the presence of large quantities of trifluoromethanesulfonic acid. The process of the Jouffret patent produces primarily hydroquinone and cannot be controlled to produce catechol. Further, Jouffret teaches that the hydroxylation will not take place satisfactorily in the presence of transitional metal ions while in the process of the present invention it is critical to have cations of transition metal ions present to control the ratio of ortho to para formed. Particularly desirable cations are vanadium, titanium, and zirconium to increase the para isomer and uranium to increase the ortho isomer.

It is convenient to load the cations onto the polymer from an aqueous solution using conventional ion exchange techniques. However, the introduction of the cations by electrophoresis through a membrane is within the scope of the present invention. It is convenient to prepare the polymeric material by exchanging part of the hydrogen ions with the desired metal in an aqueous or nonaqueous solution, separating the polymeric material from the solution and introducing the polymeric material into the reaction mixture.

Although the invention is described in greatest detail in terms of the oxidation of phenol to dihydroxybenzene, any suitable arene, alkene, or cyclic ketone may be used. The term "arene" as used herein includes substituted arenes such as anisole, phenol, mesitilene, cresols and the like. The process using phenol is particularly useful because of the control over the ratio of catechol to hydroquinone, the O:P ratio.

The solvent itself may be the reactant or any oxidatively stable solvent which will not leach the cation from the polymer may be used. Examples of such solvents are halocarbons, such as carbon tetrachloride, methylene chloride, chlorobenzene, and fluorocarbons. Other possible solvents include ethers, nitriles, esters, and sulfolane.

The temperature at which the reaction is effected is not critical. Any temperature between the freezing point of the reaction mixture and its boiling point may be used. The desirable reaction conditions are mild. At room temperature (20° C.) the oxidation proceeds at a moderate rate and increases with temperature. The possibility of hydrogen peroxide decomposition makes extremely high temperatures undesirable. Preferable temperatures range from 40° C. to 100° C. (or the refluxing temperature of the solvent).

The amount of catalyst used may vary depending on the rate of reaction desired and the loading of metal in the catalyst. The more catalyst (or the higher the metal loading) the faster the reaction proceeds.

Any ratio of the organic compound to hydrogen peroxide may be used. It is desirable to have at least equivalent amounts of the organic compound and hydrogen peroxide so that an excess hydrogen peroxide will not be present only to be wasted. An excess of the organic compound may also be used as a solvent.

The hydrogen peroxide may be added at one time or may be added gradually during the course of the reaction. It is desirable to add the hydrogen peroxide gradually to minimize side reactions and hydrogen peroxide decomposition.

An important advantage of the present invention is that it is neither necessary nor desirable to maintain anhydrous conditions in the reaction mixture which can increase both the cost of the process and create safety hazards.

It is desirable to use inexpensive and available strengths of hydrogen peroxide between 5% and 90% although any strength hydrogen peroxide may be used. It is preferable to use a 10% to 70% hydrogen peroxide to minimize the overall costs of the process, to increase the reaction yield, and to avoid the handling of the more hazardous higher strength hydrogen peroxide solutions.

It has been found possible to increase the rate of reaction by adding a carbonyl compound, such as acetone or benzaldehyde, to the reaction mixture.

The following examples are presented to illustrate the best mode of practicing the invention but are not to be construed to limit the invention to the examples.

EXAMPLES

The strongly acid form of the polymeric catalyst was prepared by adding pulverized solid Nafion (Registered U. S. Patent and Trademark Office) perfluorosulfonate polymer to concentrated nitric acid at approximately 60° C. to 80° C. and stirring for one hour, thereby converting the sulfonate groups to sulfonic acid groups. A solid form of the polymer is hereinafter referred to as "resin". The resin was separated from the acid, washed, and dried. Portions of the dried resin were contacted with a solution containing the desired cations separated and dried as illustrated by Method A or Method B procedures below. The degree of exchange of the cation was determined for several examples by exchanging samples of the resin with 1 M sodium nitrate and titrating with dilute sodium hydroxide.

(Method A)

A vanadium form of the resin was prepared by slurrying 2 g of the acid form of the resin for two hours at room temperature in 75 ml of a 1 mM solution of vanadium pentoxide in 0.3 M nitric acid. The resin was then washed and dried.

(Method B)

A titanium form of the resin was prepared by slurrying 2 g of the acid form of the resin for two hours at room temperature in 25 ml of an 80 mM solution ot titanyl acetonylacetate in ethanol. The yellow-orange powder was slurried three times in 25 ml ethanol and dried.

EXAMPLE 1

A solution of 1 g phenol in 25 ml carbon tetrachloride was added to a flask and 0.3 g of a catalyst prepared by Method A. Prior to exchange with the cation the resin contained 0.91 mmol of sulfonic acid groups per gram; after exchange with a solution of vanadium pentoxide in nitric acid, it was found that 6.9% to 7.4% of the sulfonic acid groups contained a vanadium cation. A total of 10.3 mmols of 70% hydrogen peroxide was added in four equal portions at 15 minute intervals. The catalyst turned orange-red at the first addition of hydrogen peroxide. After two hours at 40° C., 2.59 mg of hydroquinone and 0.20 mg of catechol were recovered for a catechol/hydroquinone mol ratio of 0.08.

EXAMPLE 2

A second catalyst was prepared from a resin containing 0.91 mmol sulfonic acid group per gram. The resin was charged with titanium by stirring with titanium oxide bis(2,4-pentanedioate) by Method A. It was determined that 18% of the sulfonate groups contained a titanium cation. The reaction of Example 1 was repeated and a product with a catechol/hydroquinone ratio of 0.09 was recovered.

EXAMPLE 3

A sample of catalyst was prepared as above but containing no metal cations. After 3 hours reaction, at 40° C. with 10.3 mmols of hydrogen peroxide added as a single addition, it was found that the O:P, or the catechol to hydroquinone ratio of the product was 3.19.

EXAMPLE 4

A 25 ml round bottom flask was charged with 5 g phenol, 0.8 g propylene carbonate, and 0.5 g of a vanadium-exchanged perfluorosulfonate resin, prepared by Method A. The mixture was heated to 40° C. with stirring and 10.3 mmols 70 wt % hydrogen peroxide was added in eight equal portions at 15 minute intervals. After one additional hour of stirring at 40° C., the reaction mixture was found to contain catechol and hydroquinone in the proportion listed in Table I.

EXAMPLES 5-12

The procedure of Example 4 was followed using various metal exchanged perfluorosulfonate resins as catalysts, prepared by procedures analogous to Method A or Method B. The results are listed in Table I.

EXAMPLES 13-19

The procedure of Example 4 was followed in which the concentration of hydrogen peroxide was varied thereby varying the ratio of hydrogen peroxide to water in the reaction mixture.

EXAMPLE 20

A 100 ml round bottom flask was charged with 50 ml $CH_3CN$, 2.9 g cyclooctene and 0.1 titanium exchanged perfluorosulfonate resin, prepared by Method B. The mixture was heated with stirring to reflux temperature and 20 mmol 73 wt % $H_2O_2$ was added in three equal additions at 15 minute intervals. After an additional hour of stirring the reaction was found to contain cyclooctene oxide, formed in 32% yield based on $H_2O_2$ consumed and in 73% selectivity based on cyclooctene consumed.

EXAMPLE 21

A 100 ml round bottom flask was charged with 50 ml $CH_3CN$, 2.5 g cyclohexanone, and 0.1 g titanium exchanged perfluorosulfonate resin, prepared by Method B. The mixture was heated to 80° C. with stirring, and 20 mmol 73% $H_2O_2$ was added in three equal portions at 15 minute intervals. After an additional hour of stirring, the reaction was found to contain caprolactone, formed in 16% yield based on the $H_2O_2$ consumed.

EXAMPLE 22

A strong acid ion exchange resin Amberlyst 15 (Rohm & Haas) was ion exchanged with titanium by Method B. A 25 ml round bottom flask was charged with 3 g phenol, 1 g $CH_3CN$, and 0.1 g of the titanium-exchanged resin. The mixture was heated to 60° C. and 6.4 mmol aqueous $H_2O_2$ (10% by wt) was added in nine equal portions at 15 minute intervals. After stirring for 30 minutes the mixture was found to contain catechol and hydroquinone in a ratio of 0.4 and a yield (based on $H_2O_2$) of 3%.

EXAMPLE 23

The acid groups of a titanium-exchanged resin was converted to the sodium salt by stirring one gram of the titaniumexchanged changed resin in 25 ml of a 15 mmol solution of $NaOCH_3$ in ethanol for 30 minutes. The resin was washed well with ethanol and dried in a vacuum oven at 60° C. for 30 minutes. This resin was used in the following procedure.

A 25 ml round bottom flask was charged with 3 g phenol, 1 g $CH_3CN$ and 0.1 g of the above catalyst. The mixture was found to contain catechol and hydroquinone in a ratio of 0.01 and a yield (based on $H_2O_2$) of 10%.

EXAMPLE 24

A 50 ml round bottom flask was charged with 12 g phenol, 13 ml acetone and 0.2 g titanium-exchanged perfluorosulfonate resin, prepared by Method B. The mixture was heated to 80° C. and 24 mmol $H_2O_2$ (30 wt %) was added in three equal portions at 15 minute intervals. Upon the first addition of $H_2O_2$ a very rapid reaction took place, much more rapid than in the absence of acetone. The ratio of catechol to hydroquinone was 0.02 with a yield of 6% based on the $H_2O_2$ consumed.

TABLE I
EFFECT OF DIFFERENT METALS ON CATECHOL:HYDROQUINONE MOL RATIO

| Example | Metal | O:P Mol Ratio | % Yield | Comments |
|---|---|---|---|---|
| 4 | V (V) | .8 | 10.3 | d |
| 5 | Ti (IV) | 0.1 | 1.9 | a, e |
| 6 | Zr (IV) | 1.1 | 6.2 | d |
| 7 | Mo (VI) | 0.8 | 2.6 | a, e |
| 8 | U (VI) | 4.5 | 6.8 | a, c, e |
| 9 | Cu (II) | 1.8 | 3.0 | a, b, c, f |
| 10 | Cr (III) | 2.5 | 4.8 | e |
| 11 | Co (III) | 2.8 | 4.5 | a, c, e |
| 12 | H | 2.5 | 23.9 | | a - 0.3 g catalyst used
b - 32% $H_2O_2$ used
c - 3 g phenol, 1 g propylene carbonate, 6.4 mmol $H_2O_2$
d - Method A
e - Method B
f - Method B but using $CH_3CN$ as solvent

TABLE II

EFFECT OF HYDROGEN PEROXIDE:WATER RATIO

| Example | Metal | $H_2O_2$ Water Ratio | O:P Mol Ratio | % Yield | Comments |
|---------|-------|----------------------|---------------|---------|----------|
| 13 | V  | 90:10 | 1.2  | 2.6  | a |
| 14 | V  | 70:30 | 0.8  | 10.3 | a |
| 15 | V  | 35:65 | 0.9  | 12.7 | a |
| 16 | Ti | 70:30 | 0.5  | 1.6  | a, d |
| 17 | Ti | 35:65 | 0.4  | 3.3  | a, d |
| 18 | Ti | 32:68 | 0.1  | 4.3  | b, c, d |
| 19 | Ti | 10:90 | 0.04 | 13.5 | b, c, d | a - Prepared by Method A
b - Prepared by Method B
c - 3 g phenol, 1 g $CH_3CN$, 6.4 mmol $H_2O_2$
d - T = 60° C.

What is claimed is:

1. A process for oxidizing an arene comprising contacting the arene with hydrogen peroxide in the presence of a strong-acid type cation exchange polymer wherein at least part of the cations are simple or complex cations of a transition metal.

2. The process of claim 1 wherein part of the cations of said cation polymer are hydrogen ions.

3. The process of claim 1 wherein the strong-acid type polymer contains a perfluorinated sulfonic acid moiety.

4. The process of claim 2 wherein the strong-acid type polymer contains a perfluorinated sulfonic acid moiety.

5. The process of claim 1 wherein the arene compound is a hydroxyaromatic compound.

6. The process of claim 2 wherein the arene compound is a hydroxyaromatic compound.

7. The process of claim 3 wherein the arene compound is a hydroxyaromatic compound.

8. The process of claim 4 wherein the arene compound is a hydroxyaromatic compound.

9. The process of claim 3 wherein the transition metal cation is an atom selected from the group consisting of vanadium, titanium, zirconium, and uranium and the aqueous hydrogen peroxide concentration is between 5% and 90%.

10. The process of claim 9 wherein the aqueous hydrogen peroxide concentration is between 10% and 70%.

11. The process of claim 4 wherein the transition metal cation is an atom selected from the group consisting of vanadium, titanium, zirconium, and uranium and the aqueous hydrogen peroxide concentration is between 10% and 70% by weight.

12. The process of claim 9 wherein the aqueous hydrogen peroxide concentration is between 10% and 70% by weight.

13. The process of oxidizing an arene with 5% to 90% by weight hydrogen peroxide in the presence of a strong-acid type cation exchange polymer wherein at least part of the cations are simple or complex cations of a transition metal.

14. The process of claim 13 wherein the arene is phenol and dihydroxyphenol.

* * * * *